United States Patent [19]
Donaldson

[11] Patent Number: 6,045,523
[45] Date of Patent: Apr. 4, 2000

[54] CERVICAL COLLAR

[76] Inventor: Alan Donaldson, 300 Nading Ferry Rd., Lewisville, N.C. 27023

[21] Appl. No.: 09/268,188

[22] Filed: Mar. 15, 1999

[51] Int. Cl.⁷ .................................................... A61F 5/00
[52] U.S. Cl. ...................................... 602/18; 128/DIG. 23
[58] Field of Search ................................. 602/5, 17, 18; 128/846, DIG. 23

[56] References Cited

U.S. PATENT DOCUMENTS

| | | | |
|---|---|---|---|
| Re. 32,219 | 8/1986 | Garth | 128/76 |
| 4,325,363 | 4/1982 | Berkeley | 128/75 |
| 4,413,619 | 11/1983 | Garth | 602/18 |
| 4,562,833 | 1/1986 | Pujals, Jr. | 128/75 |
| 4,782,824 | 11/1988 | Davies | 128/76 |
| 4,955,368 | 9/1990 | Heimann | 128/75 |
| 4,969,453 | 11/1990 | Heimann | 128/87 B |
| 4,987,891 | 1/1991 | Gaylord, Jr. et al. | 128/87 B |
| 5,060,637 | 10/1991 | Schmid | 602/18 |
| 5,180,361 | 1/1993 | Moore et al. | 602/18 |
| 5,215,517 | 6/1993 | Stevenson et al. | 602/18 |
| 5,230,698 | 7/1993 | Garth | 602/18 |
| 5,366,438 | 11/1994 | Martin, Sr. | 602/5 |
| 5,622,529 | 4/1997 | Calabrese | 603/18 |
| 5,624,387 | 4/1997 | McGuinness | 602/18 |
| 5,688,229 | 11/1997 | Bauer | 602/18 |
| 5,797,713 | 8/1998 | Tweardy et al. | 411/339 |

*Primary Examiner*—Michael A. Brown
*Attorney, Agent, or Firm*—Rhodes & Mason, PLLC

[57] ABSTRACT

A cervical collar to assist medical personnel in making diagnoses of neck or thoracic injuries while the patient wears the collar includes a major stiff portion of material that has anterolateral aspects of zones I, II and III of a patient's underlying neck that are transparent to visible light, upper and lower edges, sufficient flexibility to lie largely flat when not worn on a patient, an anterior portion including lateral extensions, an anterior window to permit access to the trachea for tracheotomy and a stiff chin support. A posterior portion extends from one of the lateral extensions and has vents to permit air to move from within the collar as worn to exterior thereof and an end with a patch of hook and loop fastener material. The other lateral extension has a posteriorly-extending leaf of hook and loop fastener material, so that the collar can be wrapped around the neck of the patient for installation and secured in position by engagement of the leaf of hook and loop material with the patch. Upper and lower soft portions of material that are transparent to visible light are mounted on the edges of the major stiff portion.

22 Claims, 2 Drawing Sheets

CERVICAL COLLAR

BACKGROUND OF THE INVENTION

The present invention relates generally to improved cervical collars to permit emergency medical personnel to monitor a patient's condition by observation of the neck during transport to a hospital or other health care facility, and afterwards.

The medical literature makes it plain that trauma personnel such as paramedics, nurses, and doctors can gain invaluable information about a patient's condition by viewing the patient's neck, particularly for patients with chest or neck injuries. Of course, such injuries or traumas are the very type of condition which may indicate the use of a cervical collar for protection of the spine and spinal cord, which may be injured, as well. However, the injuries to the patient may include a number of other injuries beyond spinal injuries, and installation of conventional cervical collars block the medical professionals' view of the neck and indicia of one or more of these conditions. For example, various signs of trauma can be seen from an inspection of the neck. These include ecchymosis, a swelling, or hematomas, that may result in airway obstruction. A swelling of the neck may indicate a mediastinal, esophageal, or tracheobronchial injury. In addition, the jugular vein, typically visible from the neck, if distended, may indicate an increased intrathoracic pressure as a result of a tension pneumothorax or pericardial tamponade.

Pneumothorax

A pneumothorax may be indicated by distended neck veins or by tracheal deviation, a shift of the trachea toward an uninjured side of the patient. A pneumothorax may arise from an injury to the lung, leading to accumulation of air in the pleural space and a subsequent loss of intrapleural pressure. Partial or total collapse of the lung may result.

A tension pneumothorax is a life-threatening lung injury. Air enters the pleural space when the patient inhales, but the air cannot escape when the patient exhales. As the intrathoracic pressure rises, it may collapse the lung on the side of the injury, causing a mediastinal shift that compresses the heart, great vessels, trachea, and the uninjured lung. This impedes venous return causing cardiac output to fall, and hypotension results. A tension pneumothorax may occur as a result of an open or closed chest injury. The distension of the jugular vein, if visible, may indicate a tension pneumothorax to a medical professional.

A pericardial tamponade is also a life-threatening cardiac injury in which blood collects in the pericardial sac, which surrounds the heart. As the amount of blood builds up, it exerts pressure on the heart, which can cause the heart to be less effective in pumping blood. Pericardial tamponade is evidenced by Beck's Triad, one component of which is a distended neck vein. If the medical personnel cannot see the distended vein because it is obscured by a cervical collar, this condition may not be diagnosed in time to save the patient.

In addition, flat external jugular veins may indicate hypovolemia.

Another injury a medical professional may need to diagnose is a hemothorax. A hemothorax is an accumulation of blood in the pleural space. A massive intrapleural hemorrhage of 1500 ml or more may result in a mediastinal shift, decreased venous return, and hypotension. This may be made apparent to medical personnel who can see a tracheal deviation in the neck.

In addition, blunt ruptures or tears of the lower trachea or mainstem bronchus may be caused by striking a dashboard or steering wheel, karate-type blows or clothesline-type injuries. An indicator of this type of injury is a subcutaneous emphysema in the neck, which may also occur in the face or suprasternal area. Thus, a view of the neck may provide an indicator of this type of injury.

Other injuries can occur directly to the neck. The neck is usually referred to by reference to three zones. Zone I is the area from the clavicle to the cricothyroid cartilage. Zone II is above Zone I and ends at the angle of the mandible. The third zone, Zone III, continues from the top of Zone II to the base of the skull. Signs of trauma to these zones can include a pulsatile or expanding hematoma, or a loss of normal anatomic prominence in the laryngeal region. Of course, any injury directly to the neck, such as an open wound or the like, may warrant continued scrutiny by medical personnel.

In addition, medical personnel may have had reason to access internal or external jugular intravenous access sites, and continued observation and monitoring of those sites is preferred.

In addition, there are times when the patient's condition indicates that an emergency tracheotomy or cricothyrotomy is needed. If the patient is wearing a conventional cervical collar that has an anterior opening, the medical personnel performing the procedure must peer through as well as operate through that window to have a view of the area being worked on during the procedure. Thus, there are numerous reasons why it is important, indeed critical, for medical personnel to be able to examine the neck of an injured patient in order to give adequate care.

Cervical collars have been known for years and are used to maintain the neck vertebrae in an aligned position. It is common for cervical collars to be used by paramedics and other emergency medical personnel. A patient who has suffered a trauma, such as from an automobile accident or the like, may have a neck injury, with or without numerous other possible injuries. The cervical collar is put on the patient to stabilize the neck while the patient is being transported to the hospital and within the hospital.

The following table includes examples of known collars of this type:

| U.S. Pat. No. | Inventor |
| --- | --- |
| 5,797,713 | Tweardy et al. |
| 5,688,229 | Bauer |
| 5,624,387 | McGuinness |
| 5,622,529 | Calabrese |
| 5,366,438 | Martin, Sr. |
| 5,230,698 | Garth |
| 5,215,517 | Stevenson et al. |
| 5,180,361 | Moore et al. |
| 4,987,891 | Gaylord, Jr. et al. |
| 4,969,453 | Heimann |
| 4,955,368 | Heimann |
| 4,782,824 | Davies |
| 4,562,833 | Pujals, Jr. |
| 4,325,363 | Berkeley |
| Re. 32,219 | Garth |

Most of these prior cervical collars have had marginal edges of a foam to provide conformability and comfort for the patient. Since the foam cannot be made transparent, these collars invariably obscure the medical professional's view of the neck of the patient. In addition, these collars are made of a material that is opaque, so that the medical professional cannot see through the collar to observe the condition of the patient's neck.

While the patents show that providing an opening for a tracheotomy is common, none show providing the entire, or even a substantial portion, of the collar as transparent. For example, the Gaylord, Jr. et al. patent has an opening described at column 3, lines 44–52 in a collar 10 that is formed of a flexible foam, as set forth at column 2, line 36.

The two Heimann patents disclose cervical collars that have extended clearances at the front of the neck, but there is no disclosure of using transparent material.

The Garth reissue patent, Re. 32,219, discloses a collar having an opening 30 for emergency tracheostomy at column 2, lines 22–27. Interestingly, at column 3, line 68-column 4, line 6, Garth discloses making the collar of a material that is transparent to x-rays, but does not mention transparency to visible light. The Garth '698 patent has a similar tracheal orifice 45 as described at column 3, lines 15–19. The preferred materials are listed at column 3, lines 49–55 without any mention of making them transparent to visible light.

The very recent Tweardy et al. patent discusses at column 2, lines 46–53, that the selection of material for use in producing the cervical collar is very important, without mention of making the collar transparent to visible light. Instead, as set forth at column 3, lines 6–9, Tweardy et al. indicate that it is important that the material be transparent to x-rays.

These conventional collars obscure the medical professional's view of the neck, which can have deleterious medical consequences. If symptoms of life threatening injuries are hidden by the cervical collar, which is the case with all known collars, the injury may lead to a tragic delay in the provision of medical services.

SUMMARY OF THE INVENTION

The present invention fulfills this need in the art by providing a cervical collar to assist medical personnel in making diagnoses of neck or thoracic injuries while the patient wears the collar wherein substantially the entire material of the collar is transparent to visible light.

The collar typically has a major stiff portion having upper and lower edges and upper and lower soft portions mounted on the edges of the major stiff portion. The collar preferably has anterolateral aspects of zones I, II and III of a patient's underlying neck and the anterolateral aspects are completely transparent to visible light. The major stiff portion is preferably made of Plexiglas™ that is transparent to visible light. The major stiff portion may be made of any suitable transparent material, which may include materials such as acrylic, lexan, polycarbonate, clear cellulose propionate, PETG polyester, clear PVC, amorphous polystyrene, cross-linked polystyrene derivatives, amorphous polyethylene terephthalate (aPET).

The collar may have vents to permit air to move from within the collar as worn to exterior thereof.

Desirably, the collar has an anterior window to permit access to the trachea for tracheotomy or cricothyrotomy.

Preferably, the major stiff portion is flexible enough to lie largely flat when not worn on a patient and can be wrapped around the neck of the patient for installation. In a preferred embodiment the major stiff portion has first and second ends, with hook type fastener material on the first end and loop type fastener material on the second end.

More preferably, the major stiff portion has an anterior portion with lateral extensions and a posterior portion unitary with one of the lateral extensions. The other lateral extension has a posteriorly-extending leaf of hook and loop fastener material, and the posterior portion has an end with a patch of hook and loop fastener material affixed thereto. The major stiff portion can be wrapped around the neck of the patient for installation and secured in position by engagement of the leaf of hook and loop material with the patch.

In the preferred embodiment the major stiff portion has a stiff chin support and the collar has upper and lower soft portions made of elastomeric material that is transparent to visible light.

The invention also provides a method of treating a patient with neck or thoracic injuries including installing a cervical collar that is substantially transparent to visible light on the neck of the patient, and observing the neck through the collar for indications of neck or thoracic injuries. The collar may be installed by emergency trauma personnel at a site remote from a health care facility and observations take place during transport to a health care facility. Preferably, the collar has anterolateral aspects of zones I, II and III of a patient's underlying neck and the observations are of zones I, II and III.

The method may include performing a tracheotomy through an anterior window in the collar including being guided in the tracheotomy by observing the procedure through the transparent collar.

Installation of the collar may include wrapping the cervical collar around the neck of the patient. This may include affixing hook type fastener material on a first end of the collar to loop type fastener material on a second end. Installation may include affixing a leaf of hook and loop type fastener material extending posteriorly of a lateral extension of an anterior portion of the collar to a patch of hook and loop type fastener material on a posterior portion of the collar.

The method may include performing a cricothyrotomy through an anterior window in the collar including being guided in the performance of the cricothyrotomy by observing the procedure through the transparent collar.

BRIEF DESCRIPTION OF THE DRAWINGS

These and other aspects of the present invention will become apparent to those skilled in the art after a reading of the following description of the preferred embodiment when considered with the drawings in which.

DESCRIPTION OF THE PREFERRED EMBODIMENTS

Figure 1:
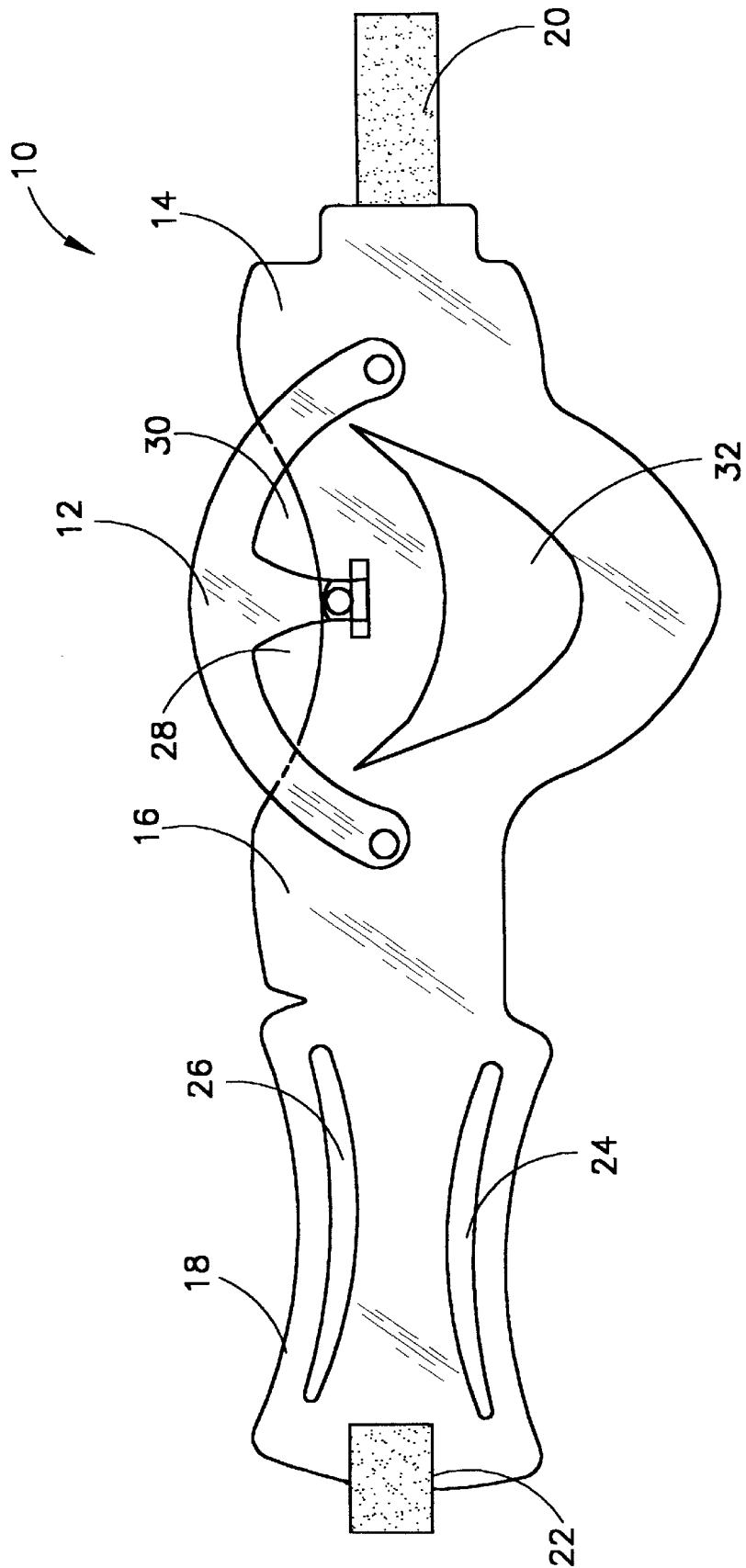
FIG. 1 is a plan view of a preferred embodiment of the invention, not installed.

FIG. 1 shows a transparent cervical collar 10 in accordance with a preferred embodiment of the invention. The collar 10 has an anterior portion 12 with lateral extensions 14 and 16. A posterior portion 18 is provided as a integral extension of the lateral extension 16. Thus, various portions 12, 14, 16 and 18 are typically made of a single piece of transparent material, so that it can generally lie flat. Of course, molding of the material is contemplated within the scope of the invention, too, to provide a more anatomical fit in accordance with any of the suitable known designs or designs which may be developed in the future. In particular, it may be desirable to mold a chin support on the anterior portion.

The lateral extension 14 has a leaf 20 hook-and-loop material, and the posterior portion 18 has a tab 22 of hook-and-loop material. Thus, when the collar is 10 is wrapped around the neck of the patient, the leaf 20 can be engaged with the tab 22 to hold the collar in place around the neck. The leaf and tab are likely not to be made of transparent material, and the arrangement so described places those obscuring elements to the rear of the patient's head, where medical personnel are unlikely to have a view anyway. The posterior portion 18 is preferably provided with vent grooves 24, 26. The anterior portion 12 is similarly provided with vent holes 28, 30 and a tracheotomy access window 32. The material of portions 12, 14, 16 and 18 must be transparent and is typically a plastic. A prototype has been made of Plexiglas™, but it is contemplated that numerous other plastics and polymers may be substituted, as long as they have the property of transparency.

Transparency is important in the areas of the collars that cover the portions of the neck where the conditions mentioned above might be occurring, so that a view of the neck portion is available to the medical personnel. If the collar has other portions which, if not transparent, would not obscure those areas, then transparency there is less critical. This is the meaning of the phrase "substantially the entire material of the collar" as used in the claims of this patent application.

The portions 12, 14, 16 and 18 are preferably fringed with a transparent, soft material such as transparent rubber so that, as they contact the soft tissue of the jaw, neck and torso, the patient is not engaged by a hard edge.

Figure 2:
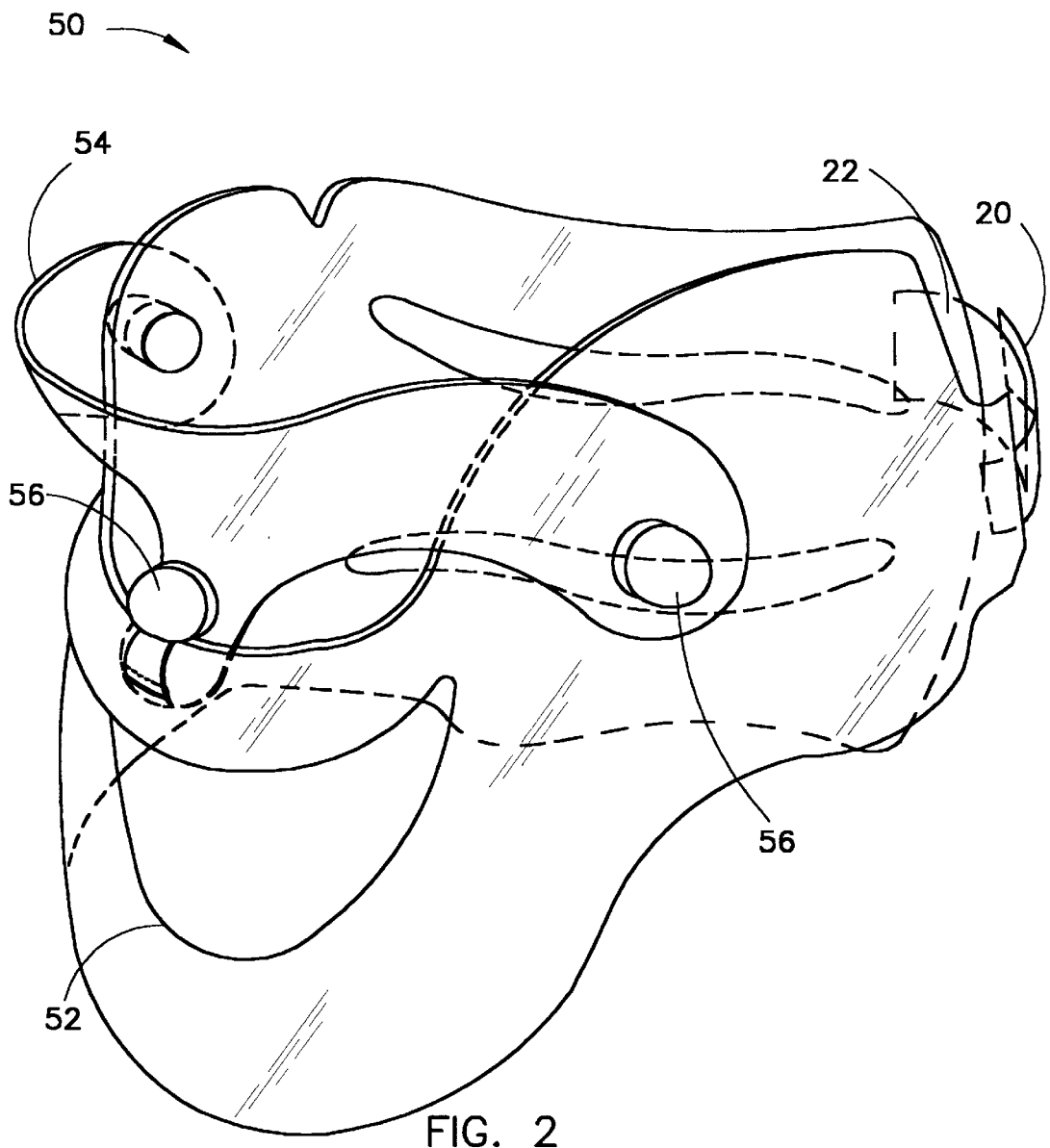
FIG. 2 is a perspective view of an alternate embodiment of the invention, configured as if, but not installed.

Referring now to FIG. 2, a second embodiment 50 of the collar can be seen. Again, the important criteria is that the collar is made of a material which is substantially entirely transparent. In this embodiment, the single piece 52 forming the anterior lateral and posterior portions of the collar omits a chin support. A separate chin support 54 is affixed to the anterior and lateral portions by plastic rivets 56, which in this case are not transparent. The use of such opaque rivets is deemed to still fall within the meaning of the term of the claims, wherein substantially the entire material of the collar is transparent to visible light.

A collar as depicted in FIG. 1 or FIG. 2 provides unobstructed views of anterolateral aspects of Zones I, II and III of the patient's underlying neck. The collar has portions which overlie those portions of the neck, this giving rise to possible identification of those portions of the collar as associated with Zones I, II and III. As can be appreciated, the stiff component of the collar provides uniform peripheral support for the head when the collar is installed, minimizing any possible movement of the head with respect to the torso, protecting the spine against injury or aggravation of injury, during trauma care.

In operation, the invention takes the form of a method of treating a patient with neck or thoracic injury. The collar is installed on the neck of the patient, and the neck is observed through the collar for indications of neck or thoracic injuries. The installation may take place at a site remote from a hospital or other health care facility. In particular, it is contemplated that the collar will be used by EMS personnel at the site of a patient's accident or injury and provide those personnel a view of the neck Zones I, II and III during transport of the patient to a health care facility.

As noted, the medical personnel can continuously monitor the neck in Zones I, II. and III for signs of internal injury. These may include tracheal deviation or shift ecchymosis, hematomas, distended jugular veins, mediastinal shift, flat jugular veins, emphysemas, and obvious neck wounds. Also, the medical personnel may continue to monitor any jugular intravenous access sites.

In the event that such a patient requires an emergency tracheotomy or cricothyrotomy, that procedure can be undertaken through the window 32, as is conventional in cervical collars. However, the medical professional is aided by the fact that the neck and the operating equipment and medical professional's hands can be seen through the collar and not merely through the window, so that it is easier for the medical personnel to perform the necessary procedure.

The collar can be installed by wrapping it around the neck of the patient and affixing the Velcro hook and loop leaf 20 to the tab 22 to secure the collar in place.

The main, stiffening part of the collar is made of a rigid material, and the upper and lower edges are preferably made of a transparent rubber. While prior cervical collars have had marginal edges of a foam, since the foam cannot be made transparent, the use of a transparent rubber or other transparent elastomeric material provides the softening contact for the patient's soft tissue while still permitting the medical personnel to see through the collar, to inspect the neck for signs of injury of the patient or for the other purposes mentioned above.

While a presently preferred material for the major stiff portion is Plexiglas™, any suitable transparent material may be substituted. Preferably, the material is flexible enough to endure the stresses involved in fitting the collar to the patient, particularly the stresses of wrapping the collar around the neck. Of course, the non-installed configuration can be made to be substantially curved, so that the amount of wrapping needed for installation can be minimized. Also, hinged portions can be included to minimize the flexibility requirements. Suitable materials may include acrylic, lexan, polycarbonate, clear cellulose propionate, PETG polyester, clear PVC, amorphous polystyrene, cross-linked polystyrene derivatives, and amorphous polyethylene terephthalate (aPET), as well as others.

Those of ordinary skill in the art will understand that the invention can be carried out using shapes and forms differing from those specifically enumerated herein, and the scope of this patent is to be determined by reference to the claims, and equivalents thereof. In particular, any suitable prior art or latterly-developed collar configuration that is made of a material that is transparent is deemed to be within the scope of the invention.

What is claimed is:

1. A cervical collar to assist medical personnel in making diagnoses of neck or thoracic injuries while the patient wears the collar wherein substantially the entire material of the collar is transparent to visible light.

2. The cervical collar of claim 1, wherein said collar has a major stiff portion having upper and lower edges and upper and lower soft portions mounted on said edges of said major stiff portion.

3. The cervical collar of claim 1, wherein said collar has anterolateral aspects of zones I, II and III of a patient's underlying neck and said anterolateral aspects are completely transparent to visible light.

4. The cervical collar of claim 1, wherein said collar has vents to permit air to move from within the collar as worn to exterior thereof.

5. The cervical collar of claim 1, wherein said collar has an anterior window to permit access to the trachea for tracheotomy.

6. The cervical collar of claim 1, wherein said collar has a major stiff portion made of a material selected from the group consisting of acrylic, lexan, polycarbonate, clear cellulose propionate, PETG polyester, clear PVC, amorphous polystyrene, cross-linked polystyrene derivatives, amorphous polyethylene terephthalate (aPET).

7. The cervical collar of claim 1, wherein said collar has a major stiff portion that is flexible enough to lie largely flat when not worn on a patient and can be wrapped around the neck of the patient for installation.

8. The cervical collar of claim 7 wherein said major stiff portion has first and second ends, with hook type fastener material on said first end and loop type fastener material on said second end.

9. The cervical collar of claim 7 wherein:
   said major stiff portion has an anterior portion with lateral extensions and a posterior portion unitary with one of said lateral extensions,
   the other lateral extension has a posteriorly-extending leaf of hook and loop fastener material, and
   said posterior portion has an end with a patch of hook and loop fastener material affixed thereto,
   so that said major stiff portion can be wrapped around the neck of the patient for installation and secured in position by engagement of said leaf of hook and loop material with said patch.

10. The cervical collar of claim 7 wherein said major stiff portion has a stiff chin support.

11. The cervical collar according to claim 7, wherein said collar has upper and lower soft portions made of elastomeric material that is transparent to visible light.

12. A cervical collar to assist medical personnel in making diagnoses of neck or thoracic injuries while the patient wears the collar comprising
   a. a major stiff portion of material that has
      i. anterolateral aspects of zones I, II and III of a patient's underlying neck that are transparent to visible light,
      ii. upper and lower edges,
      iii. sufficient flexibility to lie largely flat when not worn on a patient,
      iv. an anterior portion including lateral extensions, an anterior window to permit access to the trachea for tracheotomy or cricothyrotomy and a stiff chin support,
      v. a posterior portion extending from one of said lateral extensions and having vents to permit air to move from within the collar as worn to exterior thereof and an end with a patch of hook and loop fastener material, and
      vi. the other lateral extension having a posteriorly-extending leaf of hook and loop fastener material, so that said major stiff portion can be wrapped around the neck of the patient for installation and secured in position by engagement of said leaf of hook and loop material with said patch, and
   b. upper and lower soft portions of material that are transparent to visible light and are mounted on said edges of said major stiff portion.

13. A method of treating a patient with neck or thoracic injuries comprising installing a cervical collar that is substantially transparent to visible light on the neck of the patient, and observing the neck through the collar for indications of neck or thoracic injuries.

14. The method of claim 13 wherein the collar is installed by emergency trauma personnel at a site remote from a health care facility and observations take place during transport to a health care facility.

15. The method of claim 13 wherein the collar has anterolateral aspects of zones I, II and III of a patient's underlying neck and the observations are of zones I, II and III.

16. The method of claim 13 further comprising performing a tracheotomy through an anterior window in the collar including being guided in the tracheotomy by observing the procedure through the transparent collar.

17. The method of claim 13 wherein installation of the collar includes wrapping the cervical collar around the neck of the patient.

18. The cervical collar of claim 17 wherein installation includes affixing hook type fastener material on a first end of the collar to loop type fastener material on a second end.

19. The cervical collar of claim 17 wherein installation includes affixing a leaf of hook and loop type fastener material extending posteriorly of a lateral extension of an anterior portion of the collar to a patch of hook and loop type fastener material on a posterior portion of the collar.

20. A method of treating a patient with neck or thoracic injuries comprising:
   at a site remote from a health care facility, wrapping a cervical collar that is substantially transparent to visible light around the neck of the patient to provide a view of anterolateral aspects of zones I, II and III of a patient's underlying neck,
   affixing a leaf of hook and loop type fastener material extending posteriorly of a lateral extension of an anterior portion of the collar to a patch of hook and loop type fastener material on a posterior portion of the collar, and
   observing zones I, II and III of the neck through the collar for indications of neck or thoracic injuries during transport to a health care facility.

21. The method of claim 20 further comprising performing a tracheotomy through an anterior window in the collar including being guided in the performance of the tracheotomy by observing the procedure through the transparent collar.

22. The method of claim 20 further comprising performing a cricothyrotomy through an anterior window in the collar including being guided in the performance of the cricothyrotomy by observing the procedure through the transparent collar.

* * * * *